United States Patent [19]

Sanderson et al.

[11] Patent Number: 4,876,455
[45] Date of Patent: Oct. 24, 1989

[54] FIBER OPTIC SOLDER JOINT INSPECTION SYSTEM

[75] Inventors: Arthur C. Sanderson, Williamstown, Mass.; Lee E. Weiss; Shree K. Nayar, both of Pittsburgh, Pa.

[73] Assignee: Westinghouse Electric Corp., Pittsburgh, Pa.

[21] Appl. No.: 160,562

[22] Filed: Feb. 25, 1988

[51] Int. Cl.$^4$ ............................................. G01N 21/86
[52] U.S. Cl. ...................................... 250/560; 356/376
[58] Field of Search ................ 250/560, 561, 571, 572; 356/1, 2, 4, 369, 376, 375, 377

[56] References Cited

U.S. PATENT DOCUMENTS

| | | | |
|---|---|---|---|
| 3,976,382 | 8/1976 | Westby | 356/376 |
| 4,185,918 | 1/1980 | DiMatteo et al. | 356/375 |
| 4,238,147 | 12/1980 | Stern | 356/376 |
| 4,427,880 | 1/1984 | Kanade et al. | 250/222.1 |
| 4,452,534 | 6/1984 | Gribanov et al. | 356/359 |
| 4,472,056 | 9/1984 | Nakagawa et al. | 356/376 |
| 4,473,750 | 9/1984 | Oshida et al. | 250/560 |
| 4,508,452 | 4/1985 | DiMatteo et al. | 356/375 |
| 4,634,879 | 1/1987 | Penney | 250/560 |
| 4,650,333 | 3/1987 | Crabb et al. | 356/376 |
| 4,657,393 | 4/1987 | Stern | 356/376 |
| 4,695,163 | 9/1987 | Schachar | 356/369 |
| 4,748,335 | 5/1988 | Lindow et al. | 250/572 |

Primary Examiner—David C. Nelms
Assistant Examiner—William L. Oen
Attorney, Agent, or Firm—W. G. Sutcliff

[57] ABSTRACT

The invention is an automated solder joint inspection system for determining the quality of a specular soldered joint through examination of the shape of the joint surface using a series of point light sources and the associated highlight reflections from the joint surface. The light from the point light sources, which is directed toward the solder joint, is reflected in a pattern from the solder joint to an array of light responsive transducers, such as a camera, at a fixed location. Utilizing the intensity values from the light responsive transducer array, a binary grid map is generated for the reflections from each point light source. Using known surface features of solder joints along with curve fitting techniques, a series of grid maps may be mathematically interpreted to reconstruct the solder joint surface. A rule-based system, through comparison with acceptable solder joint surface features, evaluates and classifies the joint for an acceptability determination.

17 Claims, 6 Drawing Sheets

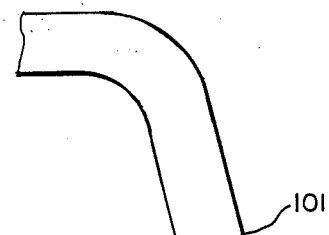
FIG. 7A.
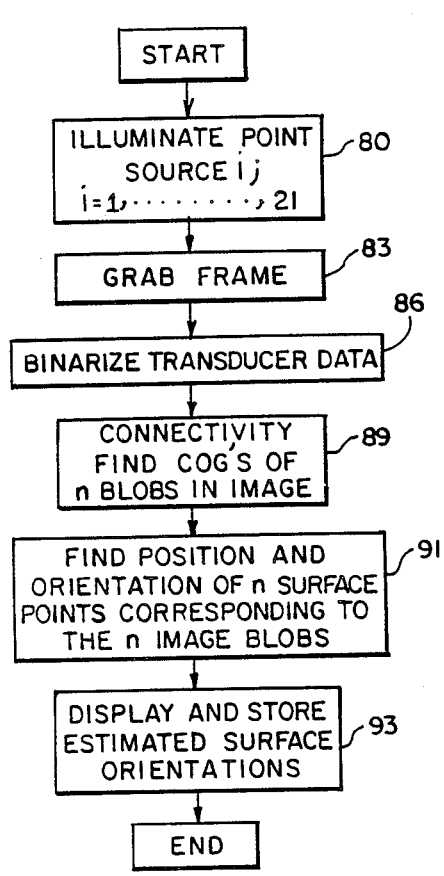
FIG. 6.
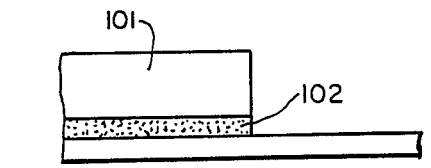
FIG. 7B.
FIG. 7C.
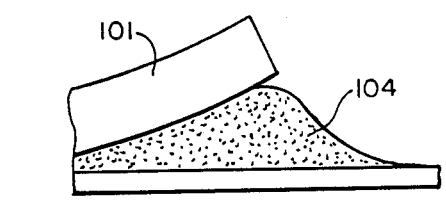
FIG. 7D.

FIBER OPTIC SOLDER JOINT INSPECTION SYSTEM

BACKGROUND OF THE INVENTION

Automated inspection of solder joints, especially those used on printed circuit boards, has become increasingly important with the proliferation of automatic electronic assembly technology. Human visual inspection is becoming less cost effective and more unreliable because of the time consuming microscopic inspection required for the typically thousands of solder joints per board. A primary feature of solder joint quality is the shape of the joint surface. Therefore the ability to automate the measurement of solder joint shapes and detect defects through shape is a significant requirement of a fully automated system. Current progress toward automated inspection includes development of optical non-contact inspection systems capable of very accurate measurements but these systems are fairly complex.

U.S. Pat. No. 4,695,163 issued on Sept. 22, 1987 to Ronald A. Schachar entitled "Method and Apparatus for Determining Surface Shapes Using Reflected Laser Light" discloses a method and apparatus for determining the surface shape of an object by scanning the object with a light beam incrementally movable in a linear and angular direction. The light beam must be directed across the surface of the object a number of times and at a multitude of angles so that light detectors may provide adequate accurate information for a determination of the surface shape. Using light beams which cover only a portion at a time of the object to be inspected, this method and apparatus provides precise information to determine surface orientations but becomes cumbersome when only an approximate profile is desired.

U.S. Pat. No. 4,508,452 issued on Apr. 2, 1985 to Paul L. DiMatteo, Joseph A. Ross, and Howard K. Stern entitled "Arrangement for Sensing the Characteristic of a Surface and Determining the Position of Points Thereon" discloses a method and arrangement for optical inspection utilizing a projector illuminating a series of predetermined sections on an object and simultaneously a camera moving about the object taking multiple photographs for subsequent analysis. The entire surface of the object is inspected and accurately mapped. No prior knowledge of the shape of the object is needed for this approach.

U.S. Pat. No. 4,427,880 issued on Jan. 24, 1984 to Takeo Kanade and Haruhiko Asada entitled "Non-Contact Visual Proximity Sensing Apparatus" teaches an apparatus for determining the location and orientation of an object utilizing a plurality of light sources spaced apart in a pattern. The light sources are directed at a symmetrical object and the reflected beams impinge on the surface of a light sensitive transducer. The pattern of these reflected beams is then analyzed to determine the location and relative orientation of the object. Note this technique does not reveal any details about the surface geometry but only the orientations and locations of an object whose geometry is already known.

FIG. 1A shows one lead 10 from a typical surface mounted flatpack semiconductor chip 11 attached with solder shown generally by 12 to a solder pad 13 on a printed circuit board 14. FIG. 1B shows the top view of this arrangement while FIG. 1C shows a cross-section view "1C—1C". For assessment of the quality of the solder joint 12 for a flatpack 11, the relevant part of the lead 10 for inspection is the underside of the foot portion 15 of the lead 10. Because the foot is positioned flat on the solder pad 13, a small amount of solder is sufficient to make a proper connection between the foot 15 and the solder pad 13. Note the meniscus 16 of solder that has been displaced from under the foot 15 to the sides and back of the foot 15. The portion of the meniscus 16 to the front of the foot 15 is the toe 17. The portion to the sides is the shoulder 18, while that portion of the meniscus to the rear of the foot 15 is the heel fillet 19. The wetting of the lead can be assessed at its true worth from the solder meniscus, however small, at all four sides of the foot 15. Further requirements on the amount of solder for flatpacks is usually not necessary. Note that further information on the assessment of solder joints may be found in "Soldering in Electronics" by R. J. Klein Wassink. FIG. 1C highlights critical features of a typical solder joint such as the toe 17, the shoulder 18, and the heel fillet 19 on a lead of a surface mounted chip on a printed circuit board. Note again the most critical solder is not apparent with visual inspection because it occurs between the bottom of the foot 15 and the top of the solder pad 13. The meniscus 16 shown by the toe 17, shoulder 18, and heel fillet 19 is indicative of the quality of that unseen solder joint. By identifying the shape of the solder meniscus and comparing this to known acceptable shapes, it is possible to determine the acceptability of the solder joint.

It is the object of this invention to provide a new method and system for determining profile information of solder joints, utilizing reflections from their specular surfaces. Using optical scanning along the surface of a solder joint, it is desired to generate a profile accurately reflecting that of the solder joint.

A more specific object of the present invention is to provide an improved method and system for surface profile determination of solder joints using a selective optical sensing such that safe, low power optical sources may be used.

Another object of the present invention is to reduce the number of data points required to determine the surface geometry of the solder joint by utilizing apriori knowledge about the salient features of the solder joint to predict the behavior of the surface in regions where data was not acquired.

Yet another object of the present invention is to compare the surface features of the object, i.e. solder joint, with typical solder joint surface features to determine joint integrity because the shape of the solder joint reveals the quality of the joint.

SUMMARY OF THE INVENTION

The invention is an automated solder joint inspection system for determining the quality of a specular soldered joint through examination of the shape of the joint surface using a series of point light sources and the associated highlight reflections from the joint surface. The light from the point light sources, which is directed toward the solder joint, is reflected in a pattern from the solder joint to an array of light responsive transducers, such as a camera, at a fixed location. Utilizing the intensity values from the light responsive transducer array, a binary grid map is generated for the reflections from each point light source. Using known surface features of solder joints along with curve fitting techniques, a series of grid maps may be mathematically interpreted to reconstruct the solder joint surface. A rule-based system, through comparison with acceptable solder joint surface features, evaluates and classifies the joint for an acceptability determination.

BRIEF DESCRIPTION OF THE DRAWINGS

The above as well as other features and advantages of this system will become apparent through consideration of the detailed descriptions in connection with the accompanying drawings in which:

FIG. 6 is the flow chart with blocks representing functional operations for determination of the solder joint shape.

FIGS. 7A, 7B, 7C and 7D show a profile of a typical solder joint and a variety of profiles that would flag the joint as defective.

DESCRIPTION OF THE PREFERRED EMBODIMENT

The inspection system in this application is based on two concepts. First, as it turns out, the surface of a solder joint is specular, that is, having a surface that ideally reflects light only at an angle of reflection equal to the angle of incidence. Consequently for highly specular surfaces such as solder joints, a bright spot of detectable intensity can be seen on the surface only if the viewing angle is the angle of reflection. This surface is contrasted to a Lambertian surface which appears equally bright from all viewing directions and reflects all incident light. A typical example of a specular surface would be a surface plated with chrome while an example of a Lambertian surface would be the surface of a piece of tissue paper. Second the features of acceptable and unacceptable solder joints are well known. This is important not only because the solder joint quality may be determined by the joint shape but also because to determine the shape of a solder joint, it is not necessary to examine the entire surface of the joint. Only enough data points are required so that critical features of the joint are revealed. Curve fitting techniques coupled with knowledge of solder joint profiles may be used to adequately overcome a deficiency that may be caused by a lack of data points.

Figure 2A:
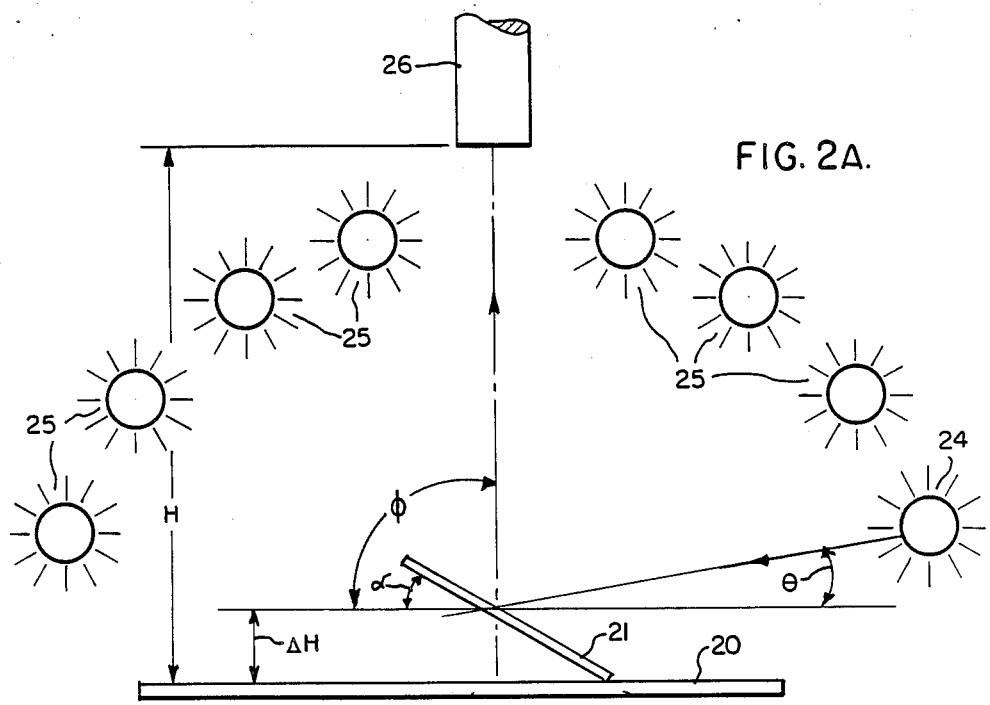
FIGS. 2A and 2B are illustrations showing the method used for determination of the surface orientation at a point on a specular surface.
Figure 2B:
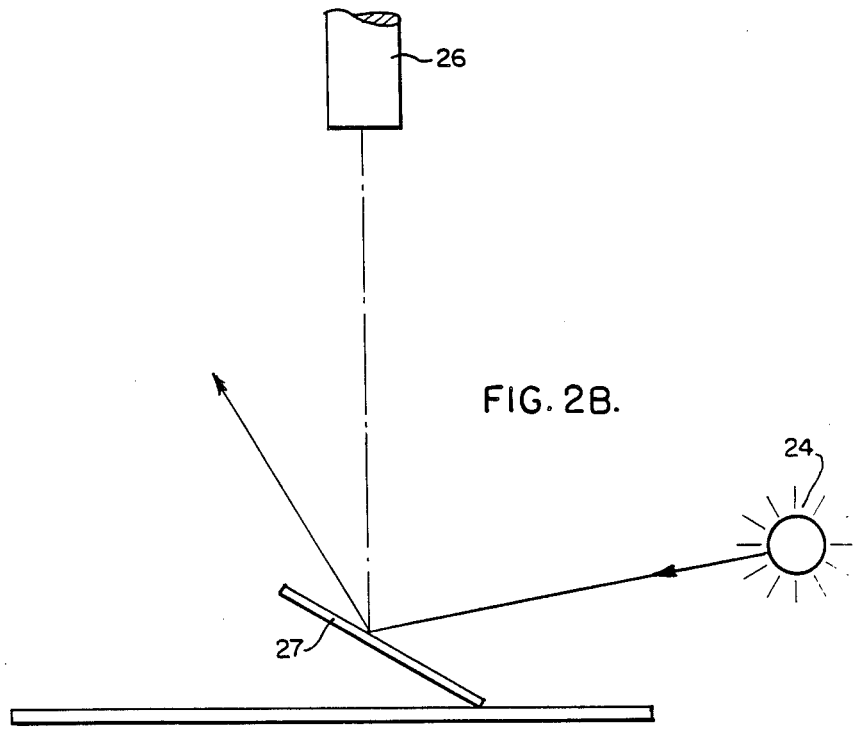

FIG. 2A shows a sketch from which the theory for the method used in determining the orientation of a surface at one point may be presented. A reference plane 20 is defined as the surface on which the object of interest 21 sits. For the application under consideration, the reference plane 20 is a printed circuit board and the object of interest 21 is the solder joint. A non-coherent light point source 24 is located at a known angle $\theta$ from the object of interest 21 such that a light ray 22 striking the object of interest 21 is reflected to a solid state camera 26. Note that if the object of interest 21 was oriented differently, as in position 27 in FIG. 2B, light from the point light source 24 would not be reflected to the camera 26. Note also the camera 26 is positioned at a known distance, H, from the reference plane 20 and $\Delta H$ is the highest point on the object from the reference plane 20. If H is much greater than $\Delta H$ then an assumption may be made that all points on the object lie on the reference plane 20. This is a key assumption because now given the angle of the point light source 24 relative to the reference plane 20 at the object of interest 21 and the angle $\phi$ between the line of sight of the camera 26 and the reference plane 20, the angle $\alpha$ of the point of interest 21 relative to the reference plane 20 may be calculated. An angle normal to the face of the object 21 from which light rays are reflected may then be determined. Positioning the point light source at different locations 25 radial to the object 21, similar information on local surface orientations over the face of the object 21 may be collected and based on this the surface of the object may be reconstructed. Note the current embodiment of the invention is capable of reconstructing only a two dimensional profile but with modifications a three dimension profile could be generated.

Figure 3:
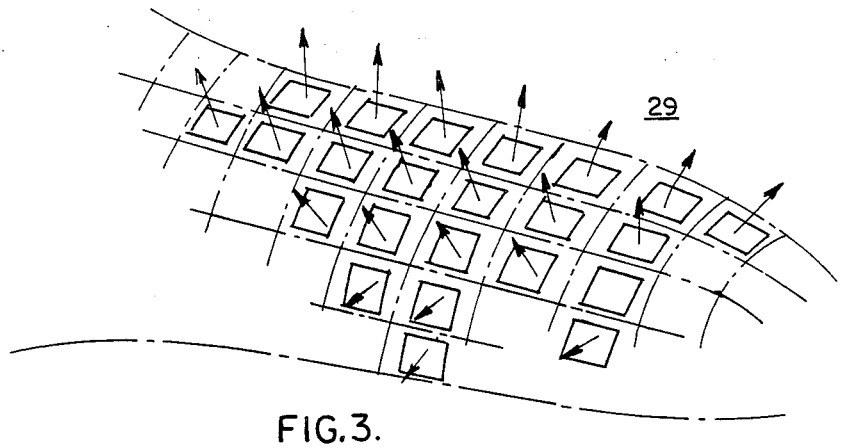
FIG. 3 is an illustration of a three dimensional reconstruction of a solder joint utilizing data from a finite number of points showing surface orientation.

FIG. 3 shows a three dimensional reconstruction of a solder joint made with knowledge of only a limited number of data points. Generally the shape of a solder joint is a continuous surface and because of this the lack of closely spaced data points across the entire surface is not critical. The gaps may be filled using general knowledge of solder joint shapes.

Figure 4:
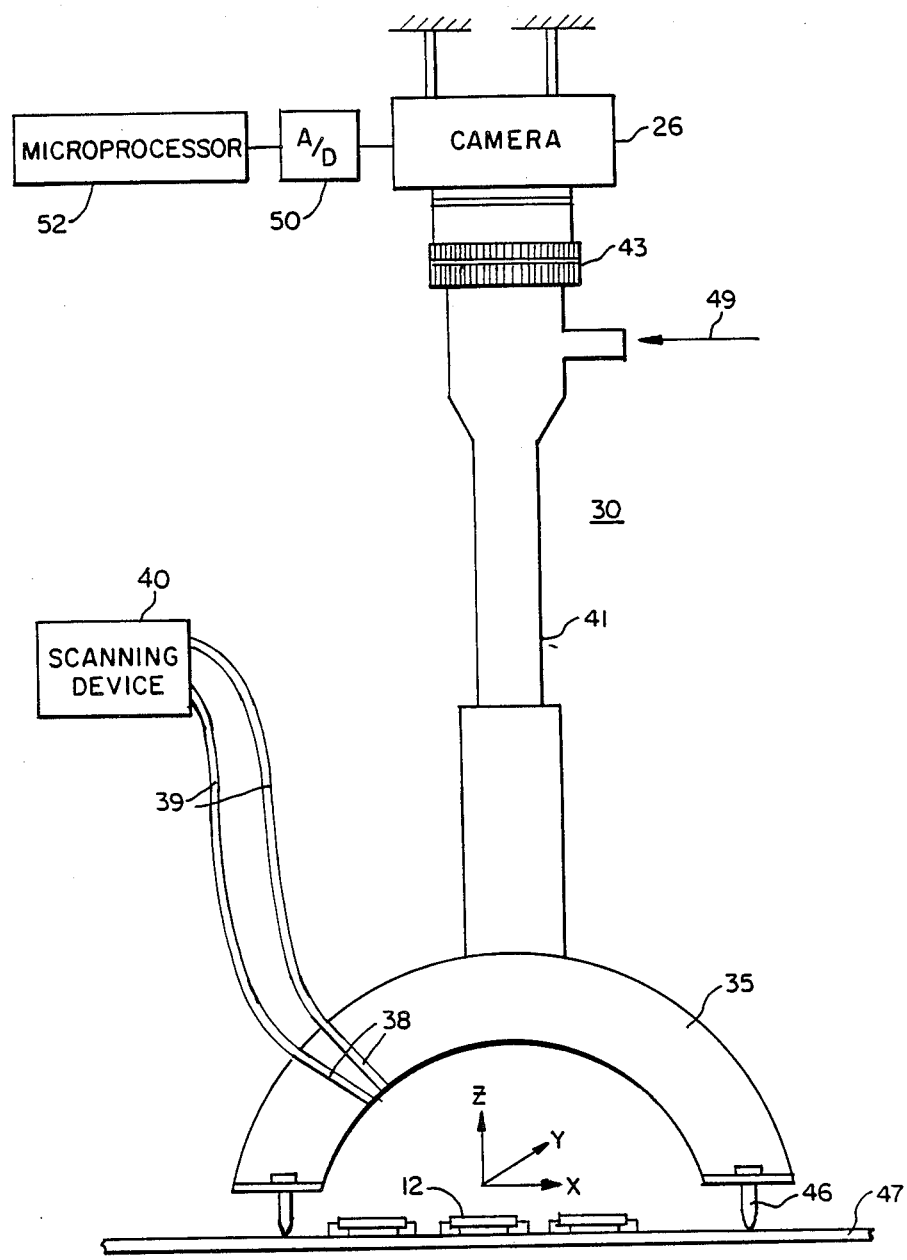
FIG. 4 is an illustration of the inspection apparatus for the determination of the solder joint surface orientation.

An embodiment of the inspection system is shown in FIG. 4. A camera 26 is supported by a structural frame (not shown) and the remainder of the system is supported by the camera 26. The camera 26, using the structural housing of an imaging device 30, supports a semicircular frame 35. The semicircular frame 35 functions to direct point light sources toward the solder joint 12 using a plurality of equally spaced radially located penetrations 38 extending from the outer diameter wall to the inner diameter wall of the frame 35. Optical fibers 39 pass through penetrations 38 and are thereby oriented such that a point light source through any fiber will illuminate the surface of the solder joint 12. An opening exists through the semicircular frame 35 and the imaging device 30 so that the camera 26 has an unobscured line of sight to the object of interest 21, which is the solder joint.

Figure 1A:
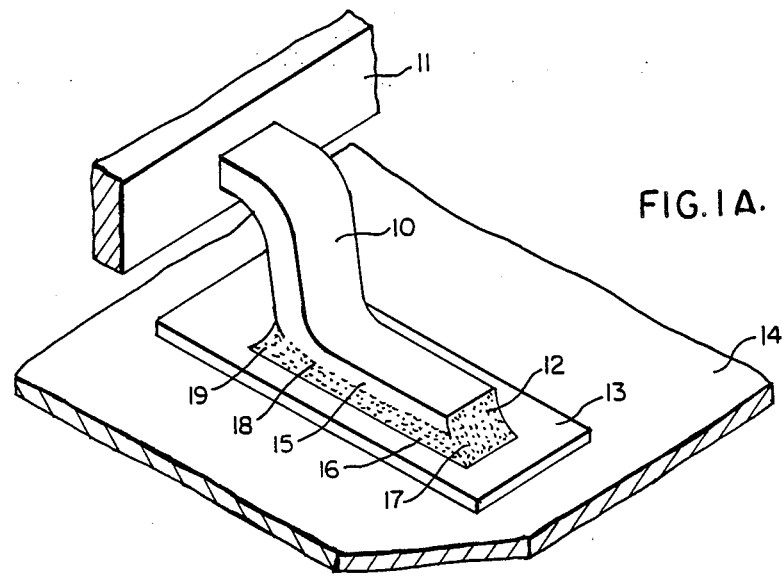
FIGS. 1A, 1B, and 1C show, respectively, a perspective view, a top view, and a cross-sectional elevation view of an enlarged portion of a surface mounted flatpack semiconductor chip attached with solder to a solder pad on a printed circuit board.
Figure 1B:
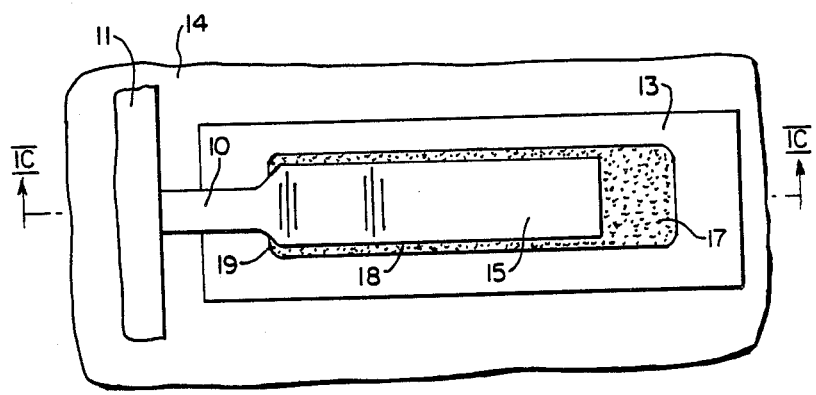
Figure 1C:
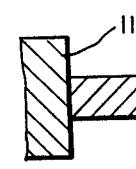
Figure 1C:
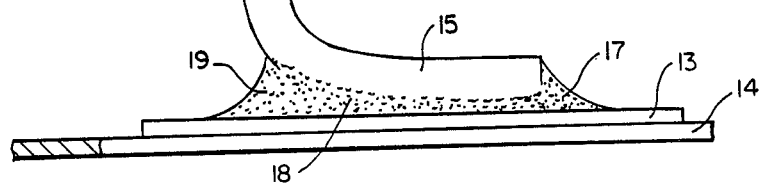

While one end of each optical fiber 39 is connected radially to the frame 35, the other end of each fiber 39 is attached to a singular electro-mechanical scanning device 40. The device 40 provides a means for selecting a particular fiber 39 and guiding a light beam into that fiber 39. The plurality of penetrations 38 and the center of the camera all are located in a single geometric plane which is coincident to the plane formed by the X-Z axes. For this reason the camera 26 will receive direct reflections from a point light source transmitted through any of the penetrations 38 but only if the reflecting surface is parallel to the Y-axis and situated directly below the camera 26. An exception to this exists because the camera lens and the point light source each have widths such that reflecting surfaces not intersected by the geometric plane or surfaces reflecting at an angle slightly deviating from the plane can still reflect light into the camera lens. As an example of the general case the flatpack chip associated with the solder joint 12 is oriented for inspection in FIG. 5 directly under the camera 26 so that the direction of the lead 15 in FIG. 1B is coincident to the projection of the X-axis directly under the frame 35. Consequently, the data accumulated for the shape of the solder joint will be data associated only with solder along a line similar to that cut by "1C—1C" in FIG. 1B, that is, associated only with the toe portion 17 (FIG. 1C) of the solder joint and not with the shoulder 18 or the heel fillet 19 since the line for inspection does not pass through either of the shoulder portions of the solder joint and the heel fillet is shielded by the lead. Note due to the width of the camera lens and point light source, solder surface slightly away from the line for inspection or surface reflecting light slightly off the geometrical plane defined above will still provide useful data.

Note that while the frame 35 permits identification of only two dimensional shapes, another geometrical configuration such as a hemisphere may be utilized with a compliment of point light sources through penetrations in the hemisphere such that information would be available to determine the three dimensional shape of a solder joint. Also note that in lieu of a hemispherical configuration, the existing frame 35 may be incrementally rotated about the Z-axis shown in FIG. 4 and equivalent data to reconstruct a three dimensional solder profile could be acquired. Using a non-rotating frame 35, the object of interest, which is the solder joint 12, could be rotated beneath the frame 35 for the same results.

Note the camera 26 may be replaced with any similar device having a means of receiving light, such as an array of light responsive transducers, and producing a grid map which indicates the light intensity across the field of view of the camera 26. The camera 26 in this embodiment may consist of a JVC type BY-110 Video Camera. Each transducer provides an analog signal representing light intensity and this signal must be digitized through a converter before the grid map may be produced. The camera 26 in this embodiment may consist of a JVC type BY-110 Video Camera, which internally converts the analog signal from the transducers in the camera to a digitized signal.

An imaging device 30, which is comprised of a thick walled tube 41 houses lenses to magnify the solder joint image for the camera 26 and is connected to the semicircular frame 35. An opening (not shown) through the frame 35 permits an unobstructed path from the upper end of the device 30 through the inside edge of the frame 35. The upper end of the device 30 is attached to the camera 26 through a coupling 43.

The imaging device 30 provides further benefits. For initial positioning of the inspection system over a solder joint and for gross visual inspection, the imaging device 30, with an independent light source 49, uses optical fibers (not shown) inserted in a plurality of circular channels bored longitudinally through the thick walled tube 41 to direct light for illumination of the solder joint. This illumination is not used in lieu of the point light sources but only as a work light. The imaging device may consist of a Scholly type 20.10145 Micro T.V. Probe 145/10 mm. Spacer calibration posts 46 attached to the bottom of the frame 35 permit the system to rest with stability upon a table 47 during set-up. After set-up the posts are retracted so the frame 35 may controllably move. One embodiment provides a movable table 47 with a means for translation and rotation such that different portions of the solder joint, such as the shoulder, may be inspected and furthermore a plurality of joints may be inspected through a process of sequential indexing.

The camera 26 in this embodiment contains a 512×512 array of light responsive transducers such that light from any one of the fibers 39 is reflected from those surfaces so oriented on the specular solder surface to the transducers. Because the solder surface is specular, that is having a smooth surface that reflects light only at the angle of reflection similar to the angle of incidence, only those surfaces that reflect light directly into the lens of the camera 26 will appear in the camera image. Each bright spot in the image, known as a highlight, is the result of a reflection from a single point on the surface of the object. Although the image captured by the camera 26 is that of the entire solder joint and any given point light source illuminates the entire solder joint, only light rays reflected from the solder joint toward the camera 26 lens will generate highlights and excite the transducers. In this manner the array of transducers will reveal those points on the solder joint 12 that have reflected light directly to the camera 26 for a specific point light source and one 512×512 grid map is generated. This provides enough information to identify the orientation of all of the points on the solder joint surface that show highlights using a specific point light source. Because the camera 26 lies in the same plane as that defined by the array of point light sources, only those surfaces with orientations parallel to the Y-axis in FIG. 5 will reflect light directly to the camera 26 from a point light source. For this reason, the capability of the system is limited by the frame 35 so that the current design provides accurate information only along, and very close to (as discussed earlier) a line shown with the plane defined by the point light source locations along the frame 35 and projected onto the solder joint 12. This is similar to the location of line A—A in FIG. 1B. Note also the current design is limited to acquiring data from reflection from surfaces whose angle $\alpha$ in FIG. 2A is less than 45°. For $\alpha$ greater than 45°, regardless of the location of the point light source 25 (assuming the source is not below the level of the solder surface), the reflected light would not reflect into the camera 26. This could be remedied by the introduction of two more cameras that would be oriented horizontally on opposite sides of the frame 35, such that one camera would be located approximately where light source 24 is shown and the other camera located directly opposite it. If only a small surface segment falls within this "unseen" area, then curve fitting techniques may be used to compensate for missing data.

The illumination of the solder joint 12 using light passing through optical fibers 38 to generate point light sources at different angles around the circumference of the frame 35 provides a sequence of 512×512 grid maps which indicate those points on the solder joint that reflect light to the camera 26. Each point light source location provides a different pattern of reflected light to the camera 26 identifying the orientation of another set of points on the solder joint 12. Through a collection of grid maps generated using point light sources from a plurality of locations around the frame 35, the orientation of a sufficient number of points on the solder joint may be accumulated so that the solder joint shape may be accurately determined.

Naturally a high degree of accuracy would require enough grid maps so that when combined the orientation of the entire surface of the solder joint would be revealed. Taking advantage of the fact that the profile of the solder joint should have an approximate shape, curve fitting techniques coupled with knowledge of the probable shape are used to fill in the gaps caused by any deficiency in information from the grid maps. Note the embodiment shown in FIG. 4 will provide enough data for only a two dimensional reconstruction of the solder joint shape. The system may be modified so that rather than having point light sources along the radius in a two dimensional path, the frame 35 could be replaced with a dome shaped configuration with associated passages for point light sources so that light could be applied and data collected to reconstruct the three dimensional shape of the solder joint.

Ideally all surfaces on the solder joint 12 will either completely reflect the light rays or not reflect them at all. In reality a reflection from a curved surface will generate a gradient of intensity. Furthermore, since the solder joint is not a totally specular surface, light will be reflected from all surfaces on the solder joint but the intensity will vary depending on the amount of reflection. In order to simplify interpretation of data provided by the grid maps, which will indicate varying levels of reflected light at different locations, it is necessary to avoid varying levels of light in favor of interpreting the transducers as either "on" or "off". For this reason an intensity threshold was established to screen the data on the grid maps so that only those pixels receiving directly reflected light would be recorded while those transducers receiving dispersed light would not be recorded. Data provided by all of the grid maps from each location of the point light source is converted from an analog to digital signal 50 and input to a microprocessor 52 where the threshold cutoff is enforced and the data is mathematically interpreted to arrive at a solder joint reconstruction.

Figure 5:
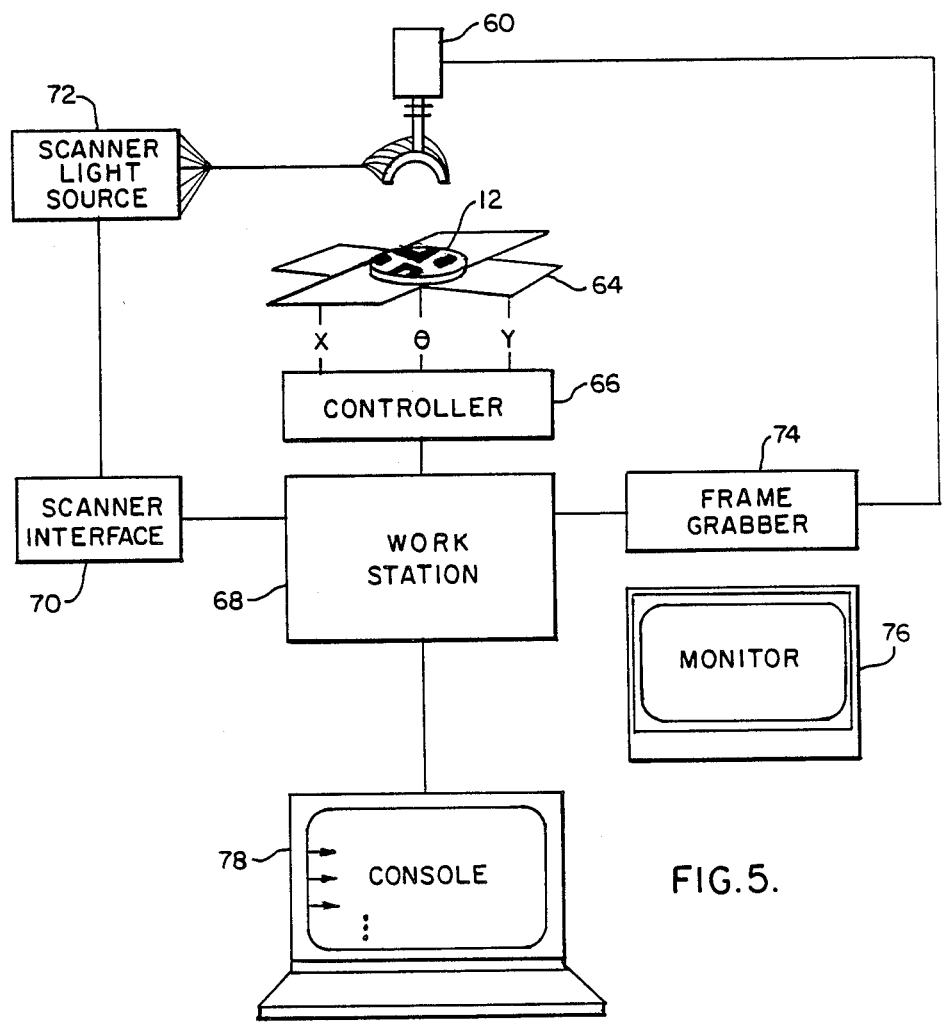
FIG. 5 is a schematic showing the inspection apparatus with supporting equipment.

FIG. 5 is a schematic of the imaging device 30 and the supporting equipment. The printed circuit board with an attached chip and solder joint 12 rest on a movable table 64. The movable table 64 is indexed using a controller 66 operated by a main workstation 68. Once the solder joint 12 is in position under the imaging device 30, a signal is sent from the workstation 68 via the scanner interface 70 to illuminate with the point light source one of the optical fibers 39 in the imaging device 30 through the scanner light source 72. With an optical fiber now illuminating the solder joint 12 surface, the camera in the imaging device 30 receives an image of the light reflected from the specular solder joint 12 surface. The reflected light excites the array of transducers (512×512) in the camera so that a frame grabber 74 records the pattern of light indicated by the pixels. Typically each transducer generates a small voltage and the voltage is recorded. This information is sent to the workstation 68 for display on a monitor 76 and for further processing 78. The further processing includes binarizing the transducer values based on a threshold discussed earlier and then, utilizing features already known about solder joints coupled with curve fitting techniques, generating a profile of the solder joint surface. With this, since the shape of a solder joint reveals the quality of the joint, certain features are inspected to determine whether or not the solder joint is defective.

FIG. 6 illustrates a flow chart for the measurement of the solder joint surfaces. With the first point source illuminated 80, the 512×512 transducer camera image is processed through a frame grabber 83, which digitizes the 512×512 array (grid map) and assigns a value to each element in the array representing light intensity at that element. This array is then converted into a binary form 86 using a threshold intensity value such that all elements in the array will be deemed either off or on depending on whether or not these individual elements meet or exceed the threshold intensity value.

With a binary array, the areas of directly reflected light may be identified and used to define areas of the solder joint oriented in the same plane. Given a group of adjacent transducers indicating directly reflected light from a given point light source, it is not necessary to separately calculate the orientation of each point on the solder surface. Instead an equivalent center of light is calculated based on the location of the reflecting surfaces. Each point on the surface that reflects is referred to as a blob and the center of gravity (COG), actually the center of light, is calculated 89 with this information on blob concentration. With this information, the surface orientation of some portions of the solder joint may be reconstructed 91. This partial map is then displayed and stored 93. Moving the point source to the second position 80, another 512×512 array of light intensity values is generated and again this information is processed to generate another map representing surface orientations. With each point source illumination, a new set of data is accumulated and processed so that after the last point source data has been accumulated, a series of grid maps exist which together provide a series of arrays representing the surface orientation of local areas across the face of the soldered joint. Note this measurement technique does not measure the absolute height of points on the surface of the soldered joint, but measures only the surface orientation. Furthermore due to a deliberate deficiency of data points the surface of the soldered joint must be reconstructed using the estimated surface orientations at different points on the surface. As the consequences of using a finite number of point sources, the surface orientation at every point on the surface cannot be measured. For this reason, curve fitting techniques must be utilized to generate a continuous solder joint profile. Note that with a greater number of point light source locations, a more comprehensive collection of data could be acquired so there may no longer be a deficiency of data. Increased point source locations however would generate an increased amount of data that would require additional processing thereby slowing the feature identification process. For this reason, a relatively low number of point light sources are used and the information available is maximized utilizing curve fitting techniques.

Just as a quality solder joint shows characteristic features, so does a defective joint. FIG. 7A shows the profile of an acceptable toe portion 100 of the solder joint relative to the lead 101 from a chip. Note the quality of the solder joint overall depends on the shoulder portion and the heel fillet as well as the toe portion. Similar profiles may be generated for these other portions and the inspection apparatus may be oriented to extract shape features of these areas as well. FIGS. 7B, 7C and 7D show a series of deviations in the toe region that may result in an unacceptable solder joint. FIG. 7B shows a "sharp toe" deviation 102 that depending on the severity, may result in an unacceptable solder joint caused by an insufficient amount of solder. FIGS. 7C and 7D show a "high toe" deviation 103 and a "toe up" deviation 104, respectively. A "high toe" deviation is indicative of excessive solder on the lead while a "toe up" deviation indicates a faulty chip lead that is not bonded with an adequate solder joint. While a multitude of potentially defective shapes exist, these figures provide a representative sampling and valid generalizations may be made based on them. The reconstructed shape of the toe portion of the solder joint is compared to the 5 different acceptable and unacceptable solder shapes to determine the quality of the solder joint at the toe. Although not shown in FIGS. 7B, 7C and 7D, various defect flags may be defined for other sections of the solder joint, such as the shoulder and the heel fillet, to highlight common flaws such that any deviation may be identified.

Figure 8:
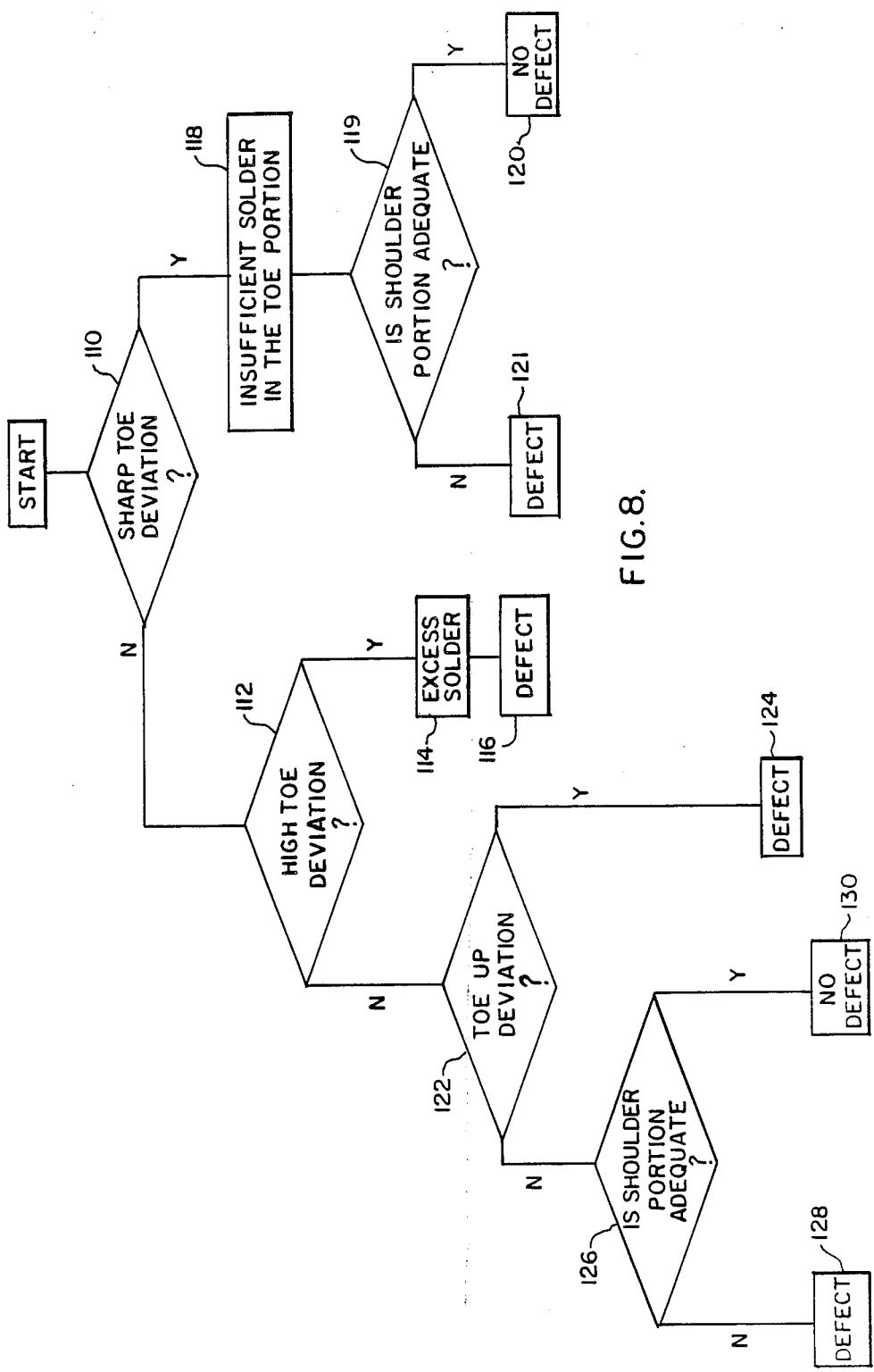
FIG. 8 illustrates a possible decision tree used in software for a rule-based computer program to evaluate the quality of a solder joint.

After the joint shape has been determined and any deviations identified, it is necessary to evaluate the deviations to determine whether or not they are sufficient to deem the joint unacceptable. A well founded determination of the solder joint integrity must be based on more than information about the toe region of the solder joint. With similar data about the acceptable and unacceptable features of the shoulder portion of the joint coupled with shape information acquired using the apparatus in this invention, a decision tree may be established to classify the solder joint. FIG. 8 illustrates a decision tree to classify the solder joint based on information from the toe region and the shoulder region of the solder joint. While the focus of FIG. 8 is the toe region of the solder joint, the decision tree is indicative of the approach used and provides a general overview for evaluating the solder joint acceptability. As an example, assume that after inspection of a solder joint using the inspection apparatus of this invention the toe portion was deemed to have a "high toe" as shown in 103 of FIG. 7C. Following the path presented in the decision tree, the toe portion would not be categorized as a "sharp toe" deviation 110, but would be under the "high toe" deviation 112. For this reason the deviation would fall into the "excess solder" category 114. Based on the concern that excessive solder will touch an adjacent lead resulting in a short circuit, generally the "excess solder" category is considered a defect 116 without further inquiry. On the other hand a "sharp toe" deviation 110, although indicative of an insufficient amount of solder at the toe 118 of the solder joint, may be offset 119 by the existence of adequate solder on the shoulder of the chip lead such that the joint is acceptable 120. Without adequate solder on the shoulder, the joint would be defective 121. Another classification addressed in the decision tree is that of the "toe up" deviation 122. A "toe up" deviation 122 essentially identifies a defective chip lead but still would involve a defective solder joint and therefore this deviation is considered a defect 124. Finally, if no deviations are identified in the toe portion of the solder joint, then the shoulder portion must still be checked 126 and depending on the adequacy of the solder on the shoulder, the joint may be acceptable 128 or defective 130. While FIG. 8 is focussed on evaluating the toe portion of the solder joint and merely mentions evaluation of the shoulder portion, the evaluation of the shoulder portion would be categorized in a similar manner using typical deviations. Similar categorization would also be done for the heel fillet of the solder joint. Considering this, it is easier to envision how the decision tree in FIG. 8 would be expanded for a more detailed evaluation of a solder joint. FIG. 8 illustrates that while a combination of deviations will likely result in an unacceptable joint, often times a singular marginal deviation may not be sufficient to deem the entire joint unacceptable. Furthermore, the decision tree illustrated in FIG. 8 may be included in a computer software program such that the entire inspection process may be automated.

While the information in FIGS. 7 and 8 may be useful for a human inspector, this information is critical for the current inspection system described in this invention. As mentioned earlier the shape features of acceptable and unacceptable solder joints are known. The process for determining the solder joint profile has been explained and automated as described. The unacceptable joint shape features, or defects, are now stored in data so that the shape features of any joint inspected by this system may be compared with defective shape features. Since singular defects or certain combinations of singular defects result in the entire joint being deemed unacceptable, a rule-based computer program utilizes the decision tree presented in FIG. 8 to determine whether or not a given joint is acceptable. Furthermore the computer program algorithm may utilize the acquired information to generate a level of confidence for each diagnosis of solder joint acceptability.

Note the system is not limited to inspection of only surface mounted flatpack semiconductor chip solder joints but may be utilized as an inspection system for any type of solder joints as long as information about the shape of the specific solder joint with acceptable and unacceptable solder joint features are known. Finally, this system may be modified slightly for inspection of many other small items having specular surfaces, such as polished machine parts.

The description of this invention is intended to be merely exemplary and not circumscriptive of the invention as it is claimed below. The invention, thus, may be modified by those skilled in the art and yet be within the scope of such claims.

We claim:
1. A method for determining the shape of an object having a specular surface comprising the steps of:
 (a) projecting sequentially toward the object the light from each of a plurality of point light sources which are arranged in a fixed configuration about a common site at which the object is placed for inspection;
 (b) viewing the object at the common site to detect light patterns caused by the reflections of light of each point light source from the object surface;
 (c) interpreting the light patterns to determine the surface orientation of points on the object surface; and
 (d) reconstructing the object surface profile using the surface orientations of points on the object.

2. The method of claim 1 wherein the projecting step utilizes light from a plurality of light sources which are arranged in a fixed arcuate two-dimensional configuration about a common site at which the object is placed for inspection.

3. The method of claim 1 wherein the projection step utilizes light from a plurality of light sources which are arranged in a fixed hemispherical configuration about a common site at which the object is placed for inspection.

4. The method of claim 1 wherein the interpreting step is comprised of converting an analog signal representing intensity into a digital signal and utilizing a threshold value to eliminate signals produced by light not directly reflected from the object surface, thereby producing a series of binary signals indicating whether or not a surface reflects light from specific point light source locations.

5. The method as defined in claim 1, further comprising, for evaluating the object, comparing the local surface features of the object profile to those of a desirable object profile.

6. The method as defined in claim 1 wherein viewing the object at the common site is done from a single direction at a fixed location.

7. The method as defined in claim 1 wherein viewing the object at the common site is done from a different singular direction at each of a plurality of fixed locations.

8. A non-contact inspection apparatus for determining the shape of an object having a specular surface comprising:
   (a) an array of point light sources spaced apart from one another in a fixed configuration about a common site at which the object is placed for inspection;
   (b) means for sequentially projecting each of the point light sources for emitting light toward the object;
   (c) a means for viewing the object at the common site to detect light patterns caused by the reflections of light of each point light source from the object surface;
   (d) a means for interpreting the light patterns to determine the surface orientation of points on the object; and
   (e) a means for reconstructing the object surface profile using the surface orientation of points on the object.

9. The apparatus of claim 8, wherein the point light sources of the array are spaced apart from one another in a fixed arcuate two-dimensional configuration.

10. The apparatus of claim 8, wherein the point light sources of the array are spaced apart from one another in a fixed hemispherical configuration.

11. The apparatus of claim 8, wherein the means for viewing the object at the common site for detecting light patterns is comprised of an array of light responsive transducers, such as a solid state camera, that produces an analog signal such as a voltage value for each transducer.

12. The apparatus of claim 8, further comprising means for comparing the local surface features of the object profile to those of a desirable profile to evaluate the object.

13. The apparatus of claim 12, wherein the object is a solder joint having a specular surface.

14. The apparatus of claim 8, wherein the means for viewing the object at the common site for detecting light patterns is comprised of an array of light responsive transducers oriented toward the object in a single direction at a fixed location.

15. The apparatus of claim 8, wherein the means for viewing the object at the common site for detecting light patterns is comprised of an array of light responsive transducers oriented toward the object from a different singular direction at each of a plurality of fixed locations.

16. A non-contact inspection apparatus for determining the shape of an object having specular surfaces comprising:
   (a) an array of point light sources spaced apart from one another in a fixed hemispherical configuration about a common site at which the object is placed for inspection;
   (b) means for sequentially activating each of the point light sources for emitting light toward the object;
   (c) means for detect the variety of light patterns caused by the reflections of light from each point light source at each location from the object surface;
   (d) means for interpret the series of light patterns to determine the surface orientation of points on the object; and
   (e) means for reconstruct the object profile using the surface orientation of a variety of points on the object.

17. A method for determining the shape of an object having a specular surface comprising the steps of:
   (a) projecting sequentially toward the object the light from each of a plurality of point light sources which are arranged in a fixed hemispherical configuration about a common site at which the object is placed for inspection;
   (b) means for viewing the object at the common site to detect light patterns caused by the reflections of light of each point light source from the object surface wherein viewing the object at the common site is done from a single direction at a fixed location;
   (c) interpreting the light patterns to determine the surface orientation of points on the object surface; and
   (d) reconstructing the object surface profile using the surface orientations of points on the object.

* * * * *